(12) United States Patent
Maier et al.

(10) Patent No.: US 11,865,033 B2
(45) Date of Patent: *Jan. 9, 2024

(54) VAGINAL PESSARY DEVICE FOR PELVIC ORGAN PROLAPSE WITH IMPROVED COLLAPSIBLE CONSTRUCTION

(71) Applicant: Reia, LLC, Lyme, NH (US)

(72) Inventors: Kaitlin E. Maier, Darien, CT (US);
Meegan P. Daigler, Portland, ME (US);
Ariana M. Sopher, Somerville, MA (US)

(73) Assignee: Reia, LLC, Lyme, NH (US)

( * ) Notice: Subject to any disclaimer, the term of this patent is extended or adjusted under 35 U.S.C. 154(b) by 435 days.

This patent is subject to a terminal disclaimer.

(21) Appl. No.: 17/331,312

(22) Filed: May 26, 2021

(65) Prior Publication Data

US 2021/0282961 A1 Sep. 16, 2021

Related U.S. Application Data

(63) Continuation-in-part of application No. 17/210,576, filed on Mar. 24, 2021, which is a continuation-in-part of application No. 16/832,839, filed on Mar. 27, 2020, now Pat. No. 11,491,047, which is a continuation-in-part of application No. 16/141,955, filed on Sep. 25, 2018, now Pat. No. 11,185,438.

(60) Provisional application No. 63/031,332, filed on May 28, 2020, provisional application No. 63/000,791, filed on Mar. 27, 2020, provisional application No.
(Continued)

(51) Int. Cl.
*A61F 6/14* (2006.01)
*A61F 6/08* (2006.01)

(52) U.S. Cl.
CPC ..................... *A61F 6/08* (2013.01)

(58) Field of Classification Search
CPC ...... A61F 6/08; A61F 6/12; A61F 6/14; A61F 6/18; A61F 2/0004; A61F 2/0009; A61F 2/0022; A61F 2/0031; A61F 2/005
See application file for complete search history.

(56) References Cited

U.S. PATENT DOCUMENTS

| 2,422,377 A | 6/1947 | Waterbury |
| 3,626,942 A | 12/1971 | Waldron |
| 4,677,967 A | 7/1987 | Zartman |

(Continued)

FOREIGN PATENT DOCUMENTS

| GB | 1121925 A | 7/1968 |
| JP | 06133996 A | 5/1994 |

(Continued)

*Primary Examiner* — Camtu T Nguyen
(74) *Attorney, Agent, or Firm* — Hinckley, Allen & Snyder, LLP; David R. Josephs

(57) ABSTRACT

A pessary providing various structures, parts, and components to enable the pessary to remain deployed in a supportive position so that it may reliably provide the desired supportive capabilities. A ridge structure prevents over-rotation of the supportive members. The pessary can be formed preferably by injection molding where the mold has at least one insert. The geometry of the pessary can enable the pessary to have the required stiffness, flexibility, hinged capability, and softness where needed to achieve a pessary that is superior to prior art pessaries.

16 Claims, 17 Drawing Sheets

Related U.S. Application Data

62/563,443, filed on Sep. 26, 2017, provisional application No. 62/827,230, filed on Apr. 1, 2019.

(56) References Cited

U.S. PATENT DOCUMENTS

| | | | |
|---|---|---|---|
| 5,014,722 | A | 5/1991 | Bauer |
| 6,503,190 | B1 | 1/2003 | Ulmsten et al. |
| 6,530,879 | B1 | 3/2003 | Adamkiewicz |
| 6,645,137 | B2 | 11/2003 | Ulmsten et al. |
| 8,127,768 | B2 | 3/2012 | Ziv |
| 8,302,608 | B2 | 11/2012 | Harmanli |
| 8,651,109 | B2 | 2/2014 | Ziv et al. |
| 8,715,244 | B2 * | 5/2014 | Prechtel ............ A61J 15/0038 604/177 |
| 8,728,013 | B2 | 5/2014 | Perle et al. |
| 8,840,598 | B2 | 9/2014 | Minoguchi et al. |
| 8,888,676 | B2 | 11/2014 | Ziv et al. |
| 8,919,345 | B2 | 12/2014 | Avery, Jr. et al. |
| 8,926,493 | B2 | 1/2015 | Karapasha |
| 9,078,726 | B2 | 7/2015 | Karapasha |
| 9,211,211 | B2 | 12/2015 | Maurette |
| 9,320,640 | B2 | 4/2016 | Durling et al. |
| 9,339,364 | B2 | 5/2016 | Durling et al. |
| 9,393,090 | B2 | 7/2016 | Karapasha |
| 9,402,703 | B2 | 8/2016 | Ziv et al. |
| 9,433,523 | B2 | 9/2016 | Avery, Jr. et al. |
| 9,439,748 | B2 | 9/2016 | Durling et al. |
| 9,555,168 | B2 | 1/2017 | Browning |
| 9,597,222 | B2 | 3/2017 | Durling et al. |
| 9,649,219 | B2 | 5/2017 | Strong et al. |
| 9,655,769 | B2 | 5/2017 | Ziv et al. |
| 9,717,582 | B2 | 8/2017 | Arcand et al. |
| 9,744,630 | B2 | 8/2017 | Avery, Jr. et al. |
| 10,039,666 | B2 | 8/2018 | Ziv et al. |
| 10,143,598 | B2 | 12/2018 | Strong et al. |
| 10,188,545 | B2 | 1/2019 | Conti |
| 10,201,411 | B2 | 2/2019 | Ramachandran et al. |
| 10,335,312 | B2 | 7/2019 | Williams et al. |
| 10,405,959 | B2 | 9/2019 | Ziv |
| 10,617,503 | B2 | 4/2020 | Rosen et al. |
| 2009/0266367 | A1 | 10/2009 | Ziv |
| 2013/0025604 | A1 | 1/2013 | Harmanli |
| 2013/0327338 | A1 | 12/2013 | Churchill et al. |
| 2016/0235583 | A1 | 8/2016 | Durling et al. |
| 2017/0100278 | A1 | 4/2017 | Ziv et al. |
| 2017/0224457 | A1 | 8/2017 | Strong et al. |
| 2018/0296387 | A1 | 10/2018 | Ziv et al. |
| 2018/0296388 | A1 | 10/2018 | Ziv et al. |
| 2019/0053937 | A1 | 2/2019 | Meyer |
| 2019/0091062 | A1 | 3/2019 | Sopher et al. |
| 2019/0336260 | A1 | 11/2019 | Price et al. |

FOREIGN PATENT DOCUMENTS

| | | |
|---|---|---|
| WO | 2004103213 A1 | 12/2004 |
| WO | 2008079271 A1 | 7/2008 |
| WO | 2017064713 A1 | 4/2017 |
| WO | 2020205614 A1 | 10/2020 |

* cited by examiner

VAGINAL PESSARY DEVICE FOR PELVIC ORGAN PROLAPSE WITH IMPROVED COLLAPSIBLE CONSTRUCTION

CROSS REFERENCE TO RELATED APPLICATION

This application claims the benefit of, and priority from, U.S. Provisional Application No. 63/031,332, entitled VAGINAL PESSARY DEVICE FOR PELVIC ORGAN PROLAPSE WITH IMPROVED COLLAPSIBLE CONSTRUCTION, filed May 28, 2020, the entirety of which is incorporated by reference herein.

This application is additionally a continuation-in-part of co-pending U.S. patent application Ser. No. 17/210,576, entitled EASILY REMOVABLE PESSARY DEVICE, filed on Mar. 24, 2021, which claims the benefit of, and priority from, U.S. Provisional Application No. 63/000,791, entitled EASILY REMOVABLE PESSARY DEVICE, filed Mar. 27, 2020, and is a continuation-in-part of co-pending U.S. patent application Ser. No. 16/832,839, entitled PESSARY FOR PELVIC ORGAN PROLAPSE, filed Mar. 27, 2020, which is a continuation-in-part of co-pending U.S. patent application Ser. No. 16/141,955, entitled PESSARY FOR PELVIC ORGAN PROLAPSE, filed Sep. 25, 2018, which claims the benefit of U.S. Provisional Application Ser. No. 62/563,443, entitled PESSARY FOR PELVIC ORGAN PROLAPSE, filed Sep. 26, 2017, and also claims the benefit of U.S. Provisional Application Ser. No. 62/827,230, entitled PESSARY FOR PELVIC ORGAN PROLAPSE, filed Apr. 1, 2019, each of which applications are incorporated herein by reference.

GOVERNMENT LICENSE RIGHTS

This invention was made with government support under a Phase I Small Business Innovation Research grant awarded by the National Institute of Health, grant application ID: 1 R43 HD097809-01 and a phase II Small Business Innovation Research grant awarded by the National Institute of Health, grant application IDs: 2 R44 HD097809-02 and 5 R44HD097809-3. The government has certain rights in the invention.

BACKGROUND OF THE INVENTION

This invention relates to pessaries for use in treating pelvic organ prolapse (POP), and more specifically, to removable pessaries.

About 50 percent of women over the age of 50 suffer from some degree of pelvic organ prolapse. The female pelvic organs include the bladder, uterus, vagina and rectum. A prolapse is a medical condition in which at least one organ of the body has collapsed forward, backward, or downward. Pelvic organ prolapse can result from weakening of the pelvic floor muscles and loss of integrity of the pelvic floor connective tissue, which allows for abnormal uterine or vaginal descent. In certain cases, the uterus or portions of the vagina can descend through the opening to the vagina. Symptoms of pelvic organ prolapse include pelvic discomfort, difficulty with urinating and voiding, and sexual dysfunction.

Contributory factors for pelvic organ prolapse can include a history of pregnancy and childbirth, advanced age, smoking, obesity, connective tissue disorders upper respiratory disorders, repetitive strain injuries, and neuropathies. The severity of pelvic organ prolapse can range from minor and asymptomatic to more severe degrees requiring medical intervention. In the latter case, women can choose to undergo reconstructive surgery to resuspend the fallen structures. As an alternative to surgery, women can manage their prolapse with a pessary. The present invention is directed to such a pessary device for non-surgical management of pelvic organ prolapse.

FIG. 1 of the prior art presents a case of pelvic organ prolapse in which certain of the pelvic organs have descended from a female pelvic region 100. The female pelvic region 100 is shown in a side view such that the front side 102 is oriented to the left and the rear side 104 is to the right. The pelvic region 100 is supported by a skeletal frame 106. A plurality of prolapsed organs 108 have descended from the pelvic region below the pelvic floor axis 109 that corresponds to a plane running from front to rear along the bottom of the pelvic region. Ordinarily, the pelvic organs are disposed above axis 109. The prolapsed organs 108 that have descended below axis 109 to include a bladder 110, a uterus 112 and the vagina 114. In the case of the vagina 114, this organ has become inverted, such that the interior lining is now an exterior surface, to the great discomfort of the person for whom it is an ordinary recessed organ. A rectum 116 remains situated above axis 109, but it is contemplated that eventually, it can descend through axis 109 to join the other prolapsed organs 108.

A pessary is a device that can be inserted into the vagina to support the descending organs. Pessaries can be recommended for women who do not wish to undergo surgery, for pregnant women, or for women with other serious health issues which makes surgery too risky. Pessaries are primarily made of medical grade silicone, with some containing internal plastic support structures for added rigidity. Some pessaries are entirely or partially made of acrylic. In function, the pessary resides in the vaginal canal and provides support for the descending organs.

For example, the pessary device of FIG. 2A (as shown inserted in FIG. 3) are attempts known in the prior art to manage and treat pelvic organ prolapse, commonly known as a "Gellhorn" pessary and "Ring with Support" pessary, respectively. The Gellhorn pessary 200 can include a knob 212 with a stem 214 extending upward and a support 216 at the upper end of the stem 214. In some embodiments, such as in the ring with the support pessary of FIG. 2B, the support 216 can include a ring 218 and drainage holes 220. This prior art pessary 200 is inserted into the vagina 114 to support the prolapsed organs 108 of FIG. 1. The pessary 200 can be placed in the vagina 114 just above axis 109 and can stay in place due to residual tone of the pelvic floor muscle group 202 and at least one of a suction, a friction force and/or larger size (so as to cause the vaginal wall to indent around the perimeter of the pessary 200). When in position, the pessary supports the organs above it and prevents them from impinging upon or passing through the vaginal introitus (opening) 204.

However, pessaries can cause erosion of the vaginal lining (epithelium) if they are inappropriately sized or left in situ for prolonged periods. To fit a pessary, a healthcare practitioner (for example, a physician, a physician's assistant, a nurse or midwife) assesses the size of the vaginal introitus 204 and depth. The pessary can be lubricated, inserted and positioned behind the pubic symphysis 206 (a bony structure in the skeletal frame 106). Pessaries in the prior art tend to be rigid and difficult to remove and re-insert by the user alone. Many women return to the practitioner every three to six months to have their pessary removed, cleaned, and replaced. Some women are able to remove and clean their pessaries themselves. The recommendations for self-cleaning have not been standardized, but for example, current pessary product inserts advise any woman who is able to remove her own pessary to remove, wash, and replace it daily. Pessaries can be cumbersome and uncomfortable to insert and remove. The average pessary user is a postmenopausal woman and these women often experience vaginal atrophy and dryness as well as narrowing of the vaginal canal and introitus, creating the potential for further difficulty and discomfort of insertion and removal. Currently available pessaries are manually folded or compressed to some degree before insertion, if possible. Although this can be helpful with enhancing the ease and comfort of the insertion, currently available pessaries are not able to significantly decrease in cross-sectional area. During removal it can be difficult to fold the pessary, often resulting in the pessary being removed in its full or close to full size and shape, which causes discomfort and difficulty. These attributes make self-maintenance of the pessary very painful, if not impossible, and consequently, few women with a pessary are able to remove, clean, and insert their own pessaries. Furthermore, some pessaries are not removable by the patient at all.

Therefore, existing pessary devices in the prior art are not easily removed and, therefore, may not address an important need for the non-surgical management and treatment of pelvic organ prolapse. While the ring with support pessary (as shown in FIG. 2B) of the prior art does contain holes (which serve the function of allowing for drainage of fluids), the holes can also be used by patients and physicians as a feature to grab for increased leverage during removal. However, the holes are located within the body of the ring pessary, making them difficult to reach. The Gellhorn prior art device has a protruding stem 214 with a knob 212, however, the stem is more for alignment once in place than for removal (as evidenced by the existence of a "short stemmed" pessary). The knob 212 is relatively small in diameter. The vast majority of patients are unable to grasp it for removal and practitioners need to use forceps to grip the knob 212 for removal. When the pessary 200 is lubricated to attempt to minimize the pain and tearing with insertion, or when it is lubricated after having been in the vagina, this further increases the difficulty of holding the pessary during both insertion and removal.

Even when pessaries are handled by a skilled practitioner, the process of removal can often be painful. Practitioners have described using forceps, that they conceal from view of the patient, to grip and remove the pessary. It can be difficult to get the proper leverage to pull out the pessary, often resulting in pain and potential tearing for the patient.

Beyond general irritation that is caused by the pessary as a foreign object in the body, the protruding, rigid knob on the existing stem can result in a pressure point when in constant contact with the vaginal wall leading to irritation, pressure sores and, in extreme cases, fistulas into the bladder or rectum.

The relative rigidity of prior art pessaries and the difficulties in removal can result in a reliance on a healthcare practitioner for regular cleaning, an inability to experience vaginal intercourse, and the pessary remaining inserted even when not necessary. It would be desirable for a pessary to be readily inserted and removed by the user, thereby improving the quality of life for that user.

Therefore, there is still a need to manage and treat pelvic organ prolapse non-surgically with a pessary, which is, as stated above, a medical device that is inserted into the vagina and acts as a shelf to support the descending organs. Due to their fixed and rigid design, current state of the art pessaries are difficult or impossible to remove and insert independently by patients. Consequently, women must rely on physicians for regular pessary cleanings, may have difficulties engaging in sexual intercourse, and must wear their pessary even when not necessary, increasing a woman's risk of developing ulcers and other avoidable complications associated with long term wear.

Moreover, a pessary that better enables self-maintenance additionally increases accessibility to prolapse management. In under resourced areas, where access to the frequent medical care needed for prolapse maintenance is difficult, a pessary that enables users to remove it and clean it themselves increases opportunity for treatment. Therefore, there is a particular need for a pessary device that can be inserted and removed easily by a non-medically trained user without the assistance of a medical practitioner.

To help address the various concerns outlined above, pessaries can be provided in a collapsible form to help aid in insertion and removal of the pessary device. However, there are many concerns as to the construction of such a collapsible pessary. For example, there is a concern with movable parts and components that would be inserted into the body. Such parts and components of the pessary must be safe and comfortable for the patient. Moreover, a pessary with such movable components must be reliably capable of collapsing and expanding when needed. Such a pessary must also be capable of being manufactured on a large scale and at reasonable cost. In addition, such a collapsible pessary must be able to control the actuation between a collapsed state and an expanded state to not only achieve proper performance of the pessary but also to ensure safety for the patient using the pessary.

SUMMARY OF THE INVENTION

The present invention preserves the advantages of prior art pessary devices, provides new advantages not found in currently available pessaries, and overcomes many disadvantages of such currently available pessaries.

The pessary of the present invention overcomes the disadvantages of the prior art by providing a pessary that can be readily inserted, removed, and cleaned without the assistance of a health or medical practitioner. The present invention provides a new and novel pessary device that improves the ease of removal of the pessary for both patients and practitioners. The pessary of the present invention includes a unique easy-to-access loop on a stem of the pessary that can fit a finger therein. The loop can be easily located by a patient so they can insert their finger therein so they may pull down on the stem to, in turn, remove the pessary. The removal loop does not rely on pinch strength for pessary removal.

The loop additionally allows practitioners to more easily locate the removal point for the pessary and eliminates the need for forceps or additional tools. The soft, silicone loop decreases the amount of pressure that the knob on the Gellhorn pessary stem typically applies to the vaginal canal because of its flexible, deformable structure.

Most notably, the present invention addresses the various concerns and disadvantages of known pessaries. The present invention provides an improved collapsible pessary that can actuate between a collapsed state and an expanded state. The pessary of the present invention provides various structures, parts, and components to enable the pessary to remain deployed in the supportive position so that it may reliably provide the desired supportive capabilities. Further, other structures, such as webbing, may be provided to prevent failure of the pessary and undesirable overcollapsing. For example, a unique ridge structure prevents over-rotation of the supportive members.

Further, various molding manufacturing techniques and methods are employed in accordance with the present invention to provide the required stiffness, flexibility, hinged capability and softness where needed to achieve a pessary that is superior to prior art pessaries. Thus, the present invention addresses the concerns as to the construction of such a collapsible pessary.

Therefore, the present invention provides a pessary device that performs better than prior art pessaries, is more reliable and is easier and more efficient to manufacture than prior art pessaries.

BRIEF DESCRIPTION OF THE DRAWING FIGURES

The novel features which are characteristic of the present invention are set forth in the appended claims. However, the invention's preferred embodiments, together with further objects and attendant advantages, will be best understood by reference to the following detailed description taken in connection with the accompanying drawings in which:

DESCRIPTION OF THE INVENTION

Figure 1:
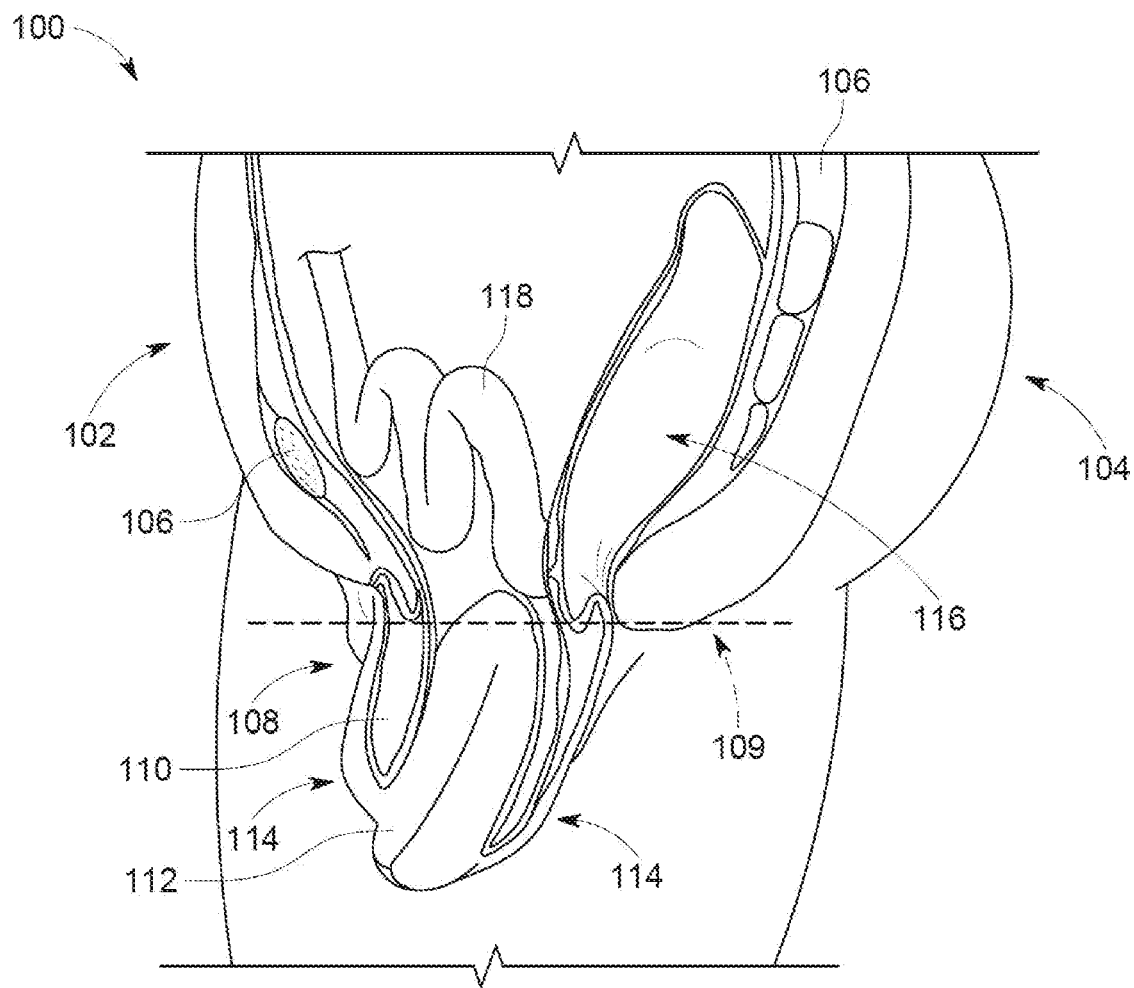
FIG. 1 is a cross sectional view of the pelvic organs in a prolapsed state, according to the prior art.
Figure 2A:
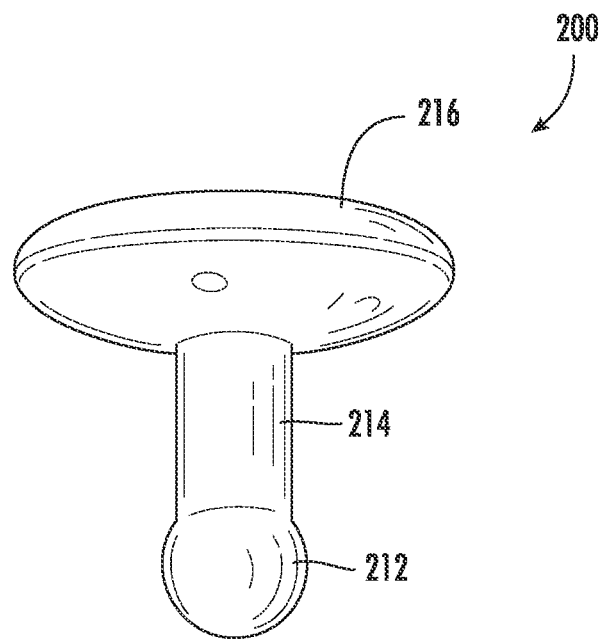
FIGS. 2A and 2B show a prior art pessary device.
Figure 2B:
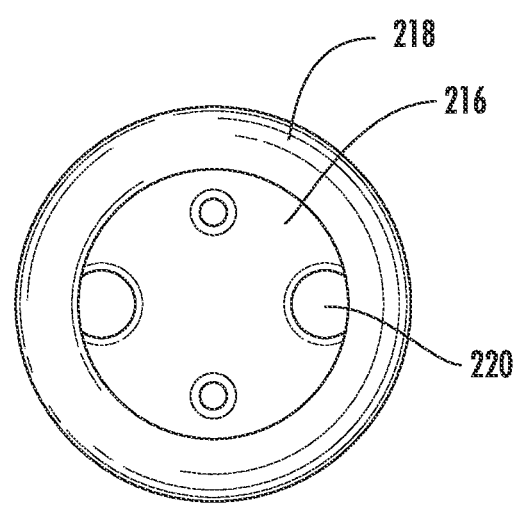
Figure 3:
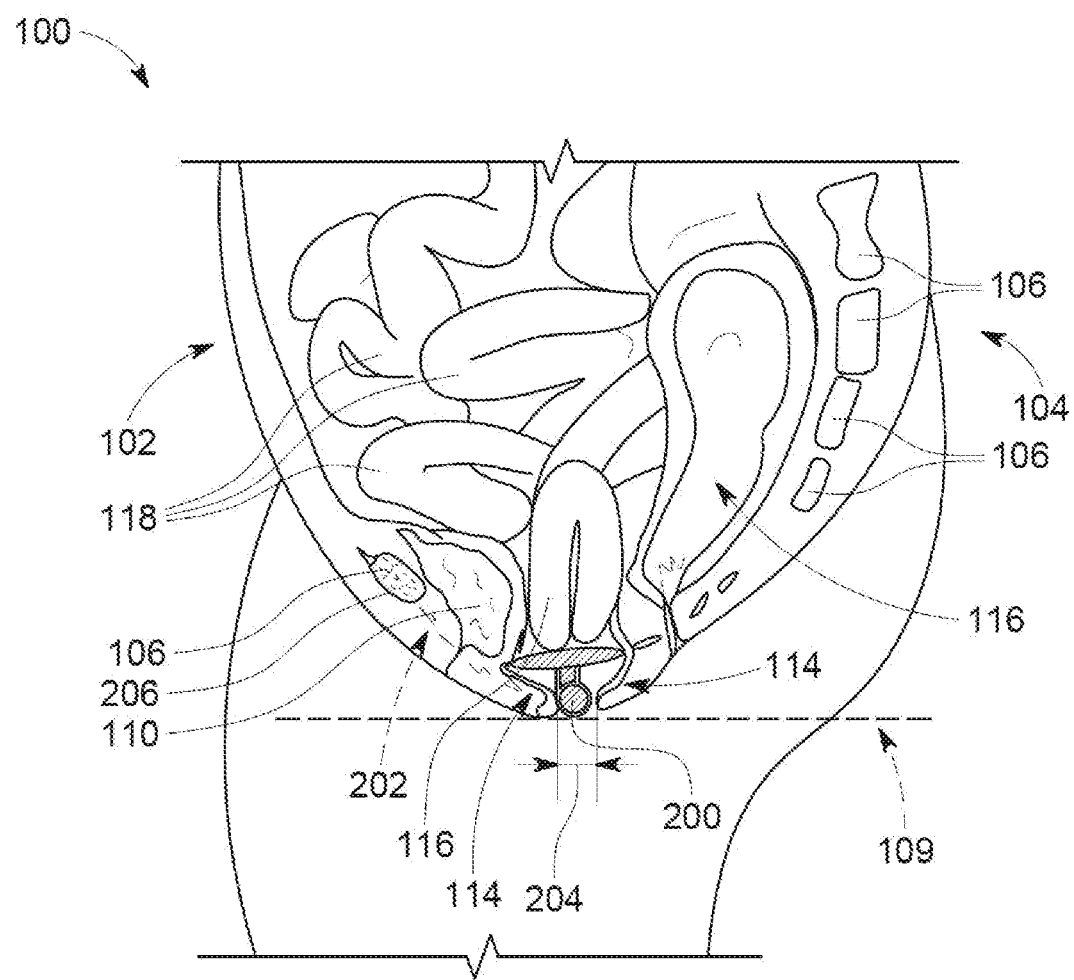
FIG. 3 shows the prior art device of FIG. 2A inserted into a patient.

Certain exemplary embodiments will now be described to provide an overall understanding of the principles of the structure, function, manufacture, and use of the device and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present disclosure. Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Further, to the extent that directional terms like top, bottom, up, or down are used, they are not intended to limit the systems, devices, and methods disclosed herein. A person skilled in the art will recognize that these terms are merely relative to the system and device being discussed and are not universal.

In accordance with the present invention, a new and novel pessary device 300 of the present invention that facilitates the removal of pessary devices is disclosed herein. Looking to the embodiment of FIGS. 4 and 5, the pessary 300 according to the present invention includes a stem 310 and supportive members 320, with a central ring or ridge, 330 disposed therebetween. The stem 310 can include a finger hold, or loop, 312 at a proximal or lower end thereof. In the illustrated embodiment, the finger hold 312 can have a maximum dimension that is greater than an outer diameter of the stem 310. At an upper end of the stem 310, a ridge or central ring 330 can extend radially outward. The stem 310 can extend distally, or upwards, towards the central ring 330. The central ring 330 can be circular and have a maximum outer diameter that is larger than outer diameter of the stem 310. The ring 330 may be continuous or discontinuous.

Figure 5:
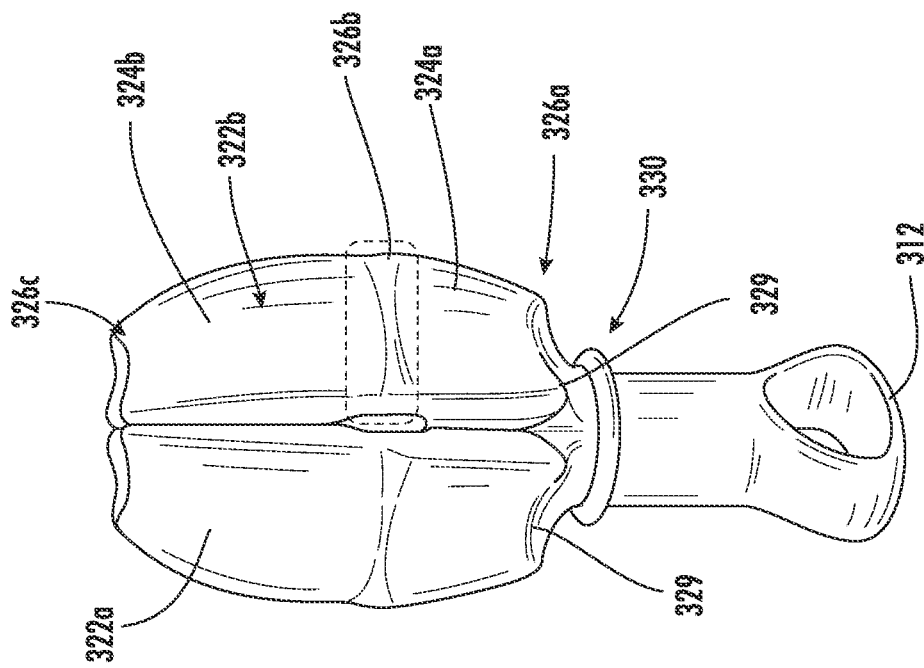
FIG. 5 shows a perspective view of the pessary of FIG. 4 in a collapsed condition.
Figure 9:
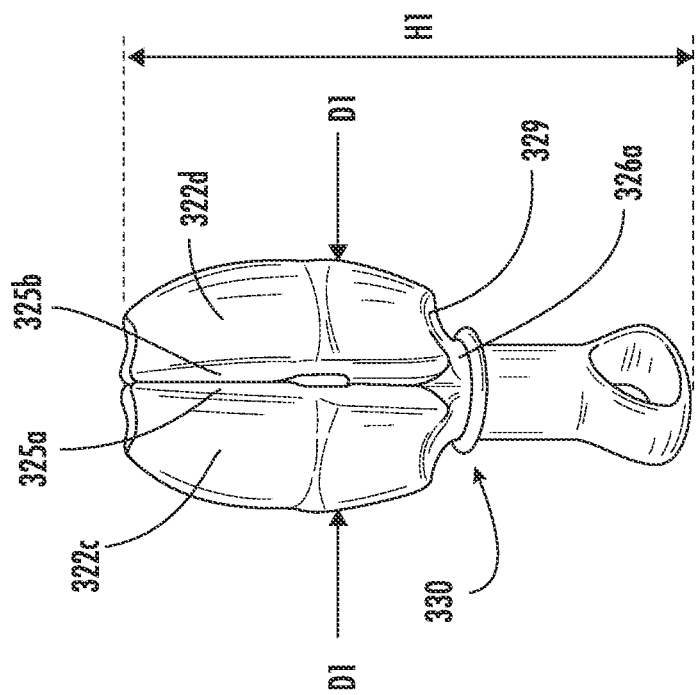
FIG. 9 is a perspective view of the pessary of FIG. 4 in a collapsed condition for installation.

The pessary 300 can be defined by a general mushroom-like shape. The top of the mushroom-like shape can be defined by the support portion 320 which includes a set of radially outwardly hinged support members 322a, 322b, 322c, 322d, as seen in FIGS. 5 and 9. The supportive member 320 in the illustrated embodiment includes four distinct members 322a, 322b, 322c, 322d that are preferably equally spaced about the circumference of the pessary 300, when viewed from the top. In an alternative embodiment, the pessary can include other numbers of petals for example three, five, six, etc. The space between support members, or petals, 322a-d can be open or enclosed by a thin membrane or other structures between the petals that can be perforated with holes, and/or formed with canals for through-drainage. Each respective support 322a-322d can include a lower support 324a and an upper support 324b. The lower support 324a can be pivotally connected, via a lower hinge 326a, to a node that extends above the central ring 330, the lower and upper supports 324a, 324b can be connected via a central hinge 326b, and the upper support 324b can be connected to an apex region 328 via a top hinge 326c. The aforementioned node can have an outer diameter that is less than the diameter of the central ring 330. Each of the support members 322a-322d can be formed having the same dimensions and construction but may be different than each other instead, if desired.

The lower and upper supports 324a, 324b can each be defined by a thicker geometry as compared to the hinges 326a-326c. The stiffness of the supportive members 320 can be defined by the thickness of the upper and lower members 324a, 324b and/or material composition. The various hinges 326a-326c of the instant design can be pivoting hinges or living hinges. In some embodiments, the hinges 326a-326c can be defined by a thinning of material to create living hinges. The supportive members 320 can be made of a rigid or semi-rigid material and the supportive members 320 and/or stem 310 can be overmolded with a soft, pliable, biocompatible material cover, such as silicone.

In a first insertion condition, as seen in FIGS. 5 and 9, the lower and upper support members 324a, 324b can be folded radially inwardly along the central hinge 326b that can cause the top apex 328 to be translated axially away from the stem 310. The first configuration, or insertion shape, of the support portion can be used during insertion as the maximum outer diameter D1 (as seen in FIG. 9) is a first, smaller, value relative to the other conditions.

Figure 7:
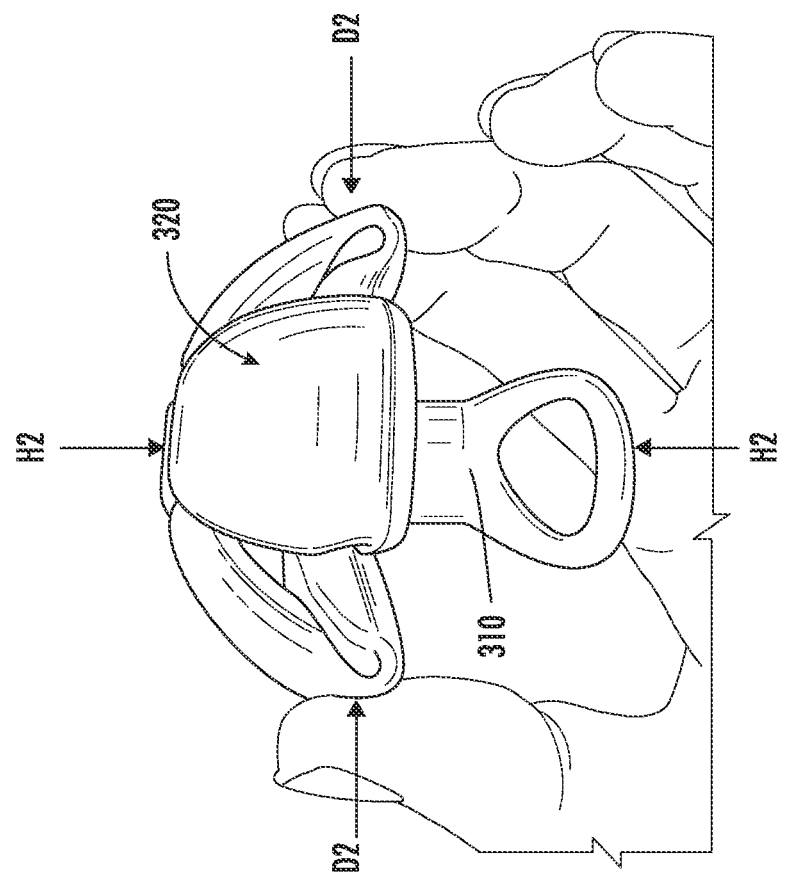
FIG. 7 is a perspective view of the pessary of FIG. 4 in an installed and locked condition.
Figure 6:
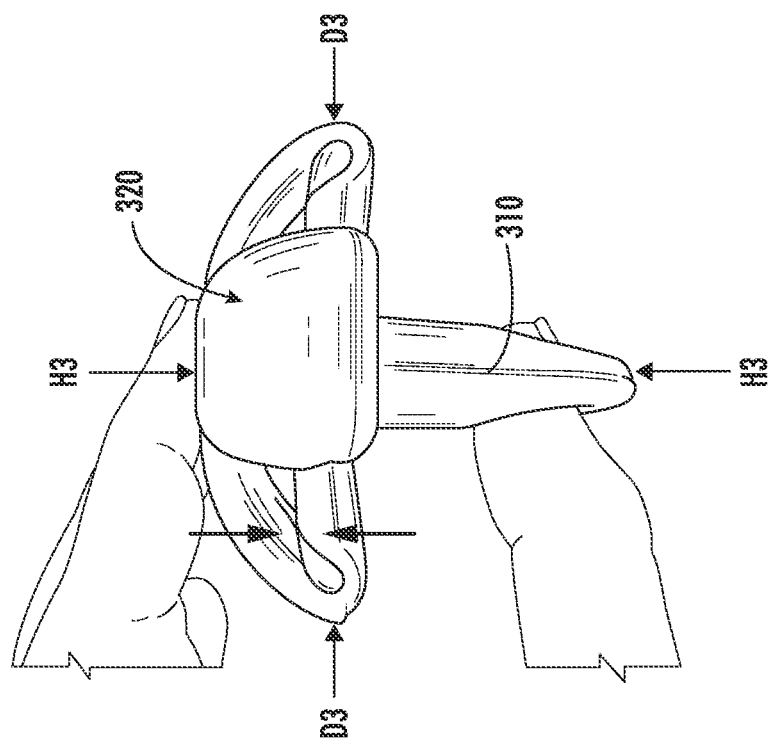
FIG. 6 is a side view of the pessary of FIG. 4.

In a second condition, or deployed orientation/shape, as seen in FIG. 7, the outer perimeter, or maximum outer diameter D2, of the support portion 320 can expand radially outward about the central hinge 326a line, relative to the central vertical axis of the pessary 300, as each of the supportive members deploy via axial force (in the direction of the apex) applied to the stem, and/or a downward axial force applied to the apex (such as from prolapse), and/or internal spring bias. In the second condition, the maximum outer diameter D2 is a second value that is larger than the first maximum outer diameter D1 value. Further, in the second condition, the overall height H2, as seen in FIG. 7, of the support portion has a second height that is less than the first height H1 of the pessary 300 in the first configuration, as seen in FIG. 9. Of importance, when the pessary 300 is being changed from the first condition to the second condition, the support portion 320 passes through an intermediate condition, as seen in FIG. 6, having a maximum outer diameter D3 that is larger than the first diameter D1 of the first condition and the second diameter D2 second condition. The movement from the intermediate condition to the second condition provides for a locking arrangement due to the maximum outer diameter D2 in the second configuration being less than the outer diameter D3 of the pessary in the intermediate condition, as seen in FIGS. 6 and 7. It is important to understand that the three heights H1, H2, H3 identified herein are defined from as a height from the top most part of the support portion 320 to the bottom most part of the stem 310.

Figure 8:
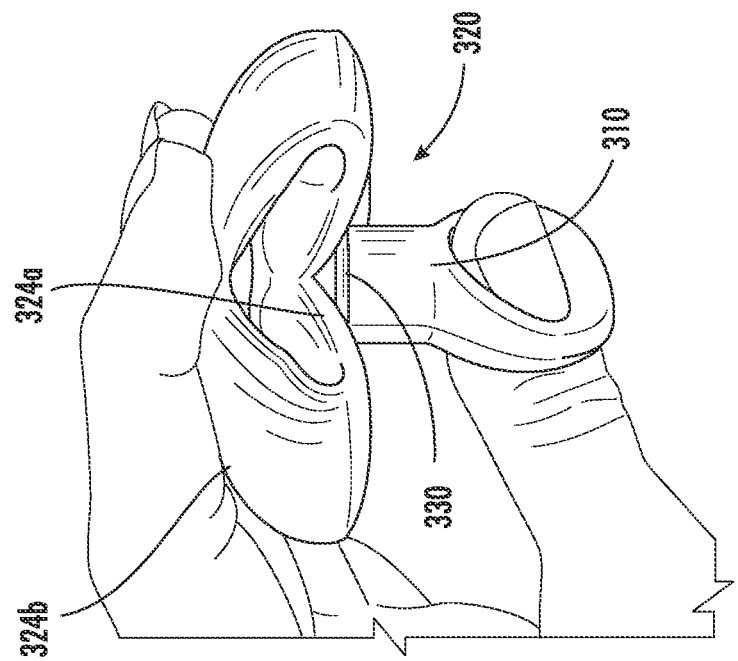
FIG. 8 is a perspective view of the pessary of FIG. 4 in an intermediate condition.

As best seen in FIGS. 8 and 9, the bottom hinge 326a is free to rotate the supportive members 324a, 324b down towards the stem 310, however the pessary 300 includes a center ring or ridge 330 just below the lower support members 324a which can help to prevent the bottom hinge 326a from over rotating the lower support members 324a too far down in the second condition. For example, an arc-shaped surface 329 can be complimentary to the radius of curvature of the ridge 330 so that the arc-shaped surface 329 can rest against the ridge 330. The center ring 330 can protrude around the diameter of the stem 310 and fits into a joint bounded by the arc-shaped surface 329 of the bottom hinge 326a, filling in the space where material was removed, or was not present, to create the bottom hinge 326a. If there is downward force on the pessary 300 (such as from a prolapse), the upper support members 324b will flatten onto the respective lower support members 324a, as seen in FIG. 8, and when the lower support members 324a start to deform down, the ridge 330 prevents the lower support members 324a from rotating any further. This allows the pessary 300 to remain supportive.

Figure 4:
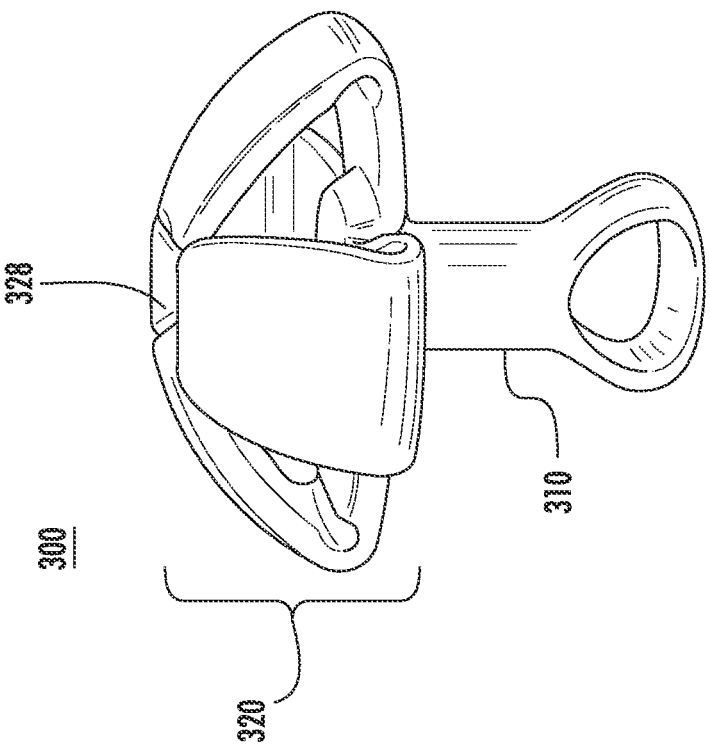
FIG. 4 shows perspective view of a pessary in a deployed/expanded condition according to a first embodiment of the present invention.

Stated another way, as shown in FIGS. 4 and 5, the central hinge 326b can be configured such that until a downwards force is applied to the top apex 328 of the pessary 300, the edges 325a, 325b of successive upper and lower support members 324a, 324b can be in contact with each other, as in FIG. 9, so the pessary 300 remains elongated for insertion purposes. Further, during insertion, the apex region 328 of the pessary 300 can be pressed against the prolapse while an upward force is applied to the stem 310. The upward force on the stem 310 can press the top 328 of the pessary 300 against the prolapse, this compressive force can cause a radially outward force on the central hinge 326b, causing the lower and upper support members 324a, 324b to rotate inward towards each other, as seen in FIG. 6. Once an inward face of the respective lower and upper support members 324a, 324b are in contact with one another, a radial force on the outer diameter of the pessary such as the vaginal walls, can cause the lower supports 324a to "draw" the stem 310 up towards the apex 328 and "lock" into a secure dome structure rather than elongate into an unsupportive state, as seen in FIG. 7.

In one preferred embodiment, the entire pessary 300 can be made of a unitary piece of material, such as uniform durometer silicone. However, it is also envisioned that the pessary 300 may be made of different components that are of the same or different materials, such as materials of multiple silicone durometers. In one exemplary embodiment, the unitary design of the instant pessary 300 can be molded as a single piece of material, as will be discussed below. In some embodiments, additional manufacturing steps can be performed, such as subtractive manufacturing steps to smooth or remove sharp edges, or other unwanted portions of material. Further, in some embodiments, the pessary can be manufactured out of two or more pieces of material. It is understood that other materials can be used and still be within the scope of the present invention.

Various locking arrangements can be provided between the supportive members 322a-322d to prevent undesired collapse during wearing, which can be overcome by an axial pulling action on the stem 310. To assist in locking the support structure 320 into the second condition once inserted into the user, the lower support members 324a of the petals are preferably downwardly arched, as shown in FIGS. 6 and 8. Due to the downward arch of the lower support 324a, the central hinges 326b are further from the apex 328 than the lower hinges 326a in the deployed state, or second configuration, as seen in FIG. 7, such that the pessary gets wider, as seen in FIG. 6, before getting narrower when moving from the deployed state (FIG. 7) to the collapsed condition (FIG. 5). The lower hinges 326a can be spring-loaded to maintain this deployed shape naturally, as seen in FIG. 7. The second configuration, or deployed shape, has a shape that has resistance to collapsing, or elongating, into the first configuration and tends to remain deployed when inward radial pressure is applied from the vagina, for example. More particularly, the lower and upper support members 324a, 324b can bottom-out on each other when radially inward pressure is applied and the stem 310 is "drawn" up. However, upon application of a downward, pulling force on the stem 310, the locking force can be overcome and the pessary 300 can collapse to the smaller diameter D1 by way of the support structure 320. The resting state of the pessary 300 is when it is substantially domed, as seen in FIG. 7, and once inserted, the device 300 deploys to this naturally supportive condition.

Figure 11:
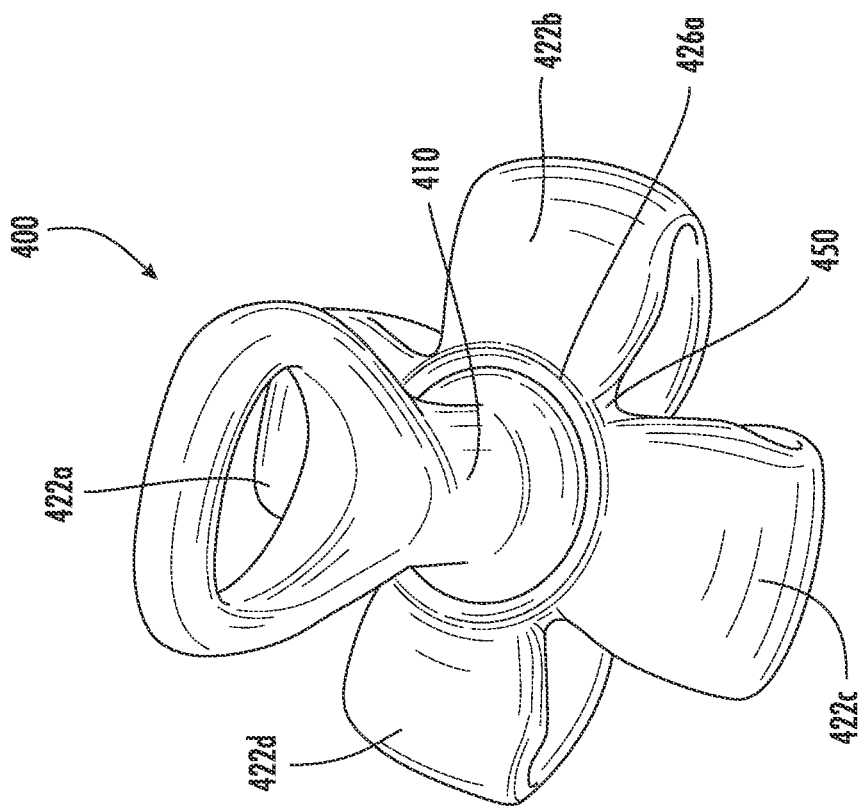
FIG. 11 is a bottom perspective view of the pessary of FIG. 10.
Figure 10:
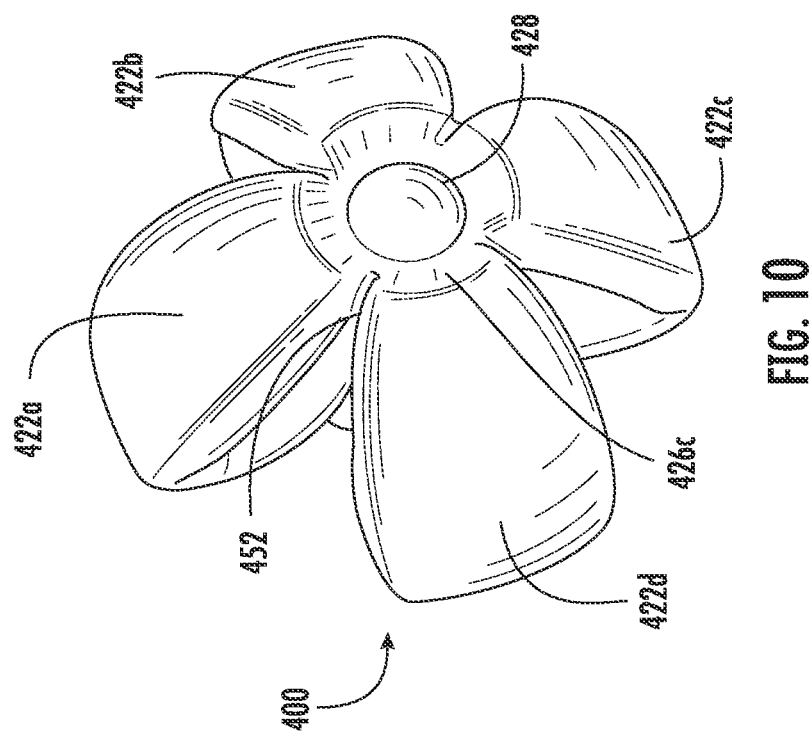
FIG. 10 is a perspective view of another exemplary embodiment of the present invention.
Figure 12:
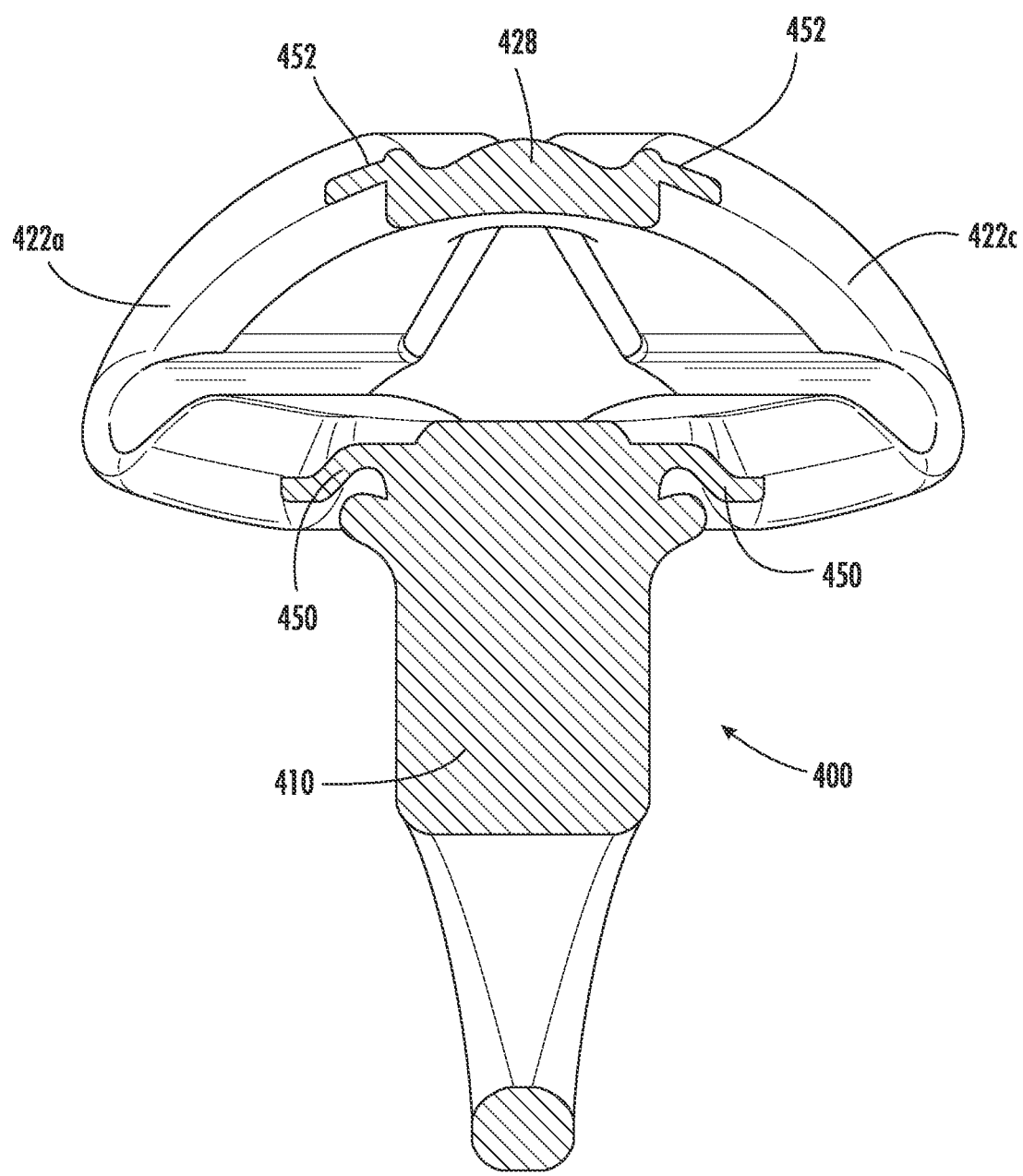
FIG. 12 is a cross-sectional view of the pessary of FIG. 10.
Figure 13:
FIG. 13 is a perspective view of a pessary in an over-collapsed condition.
Figure 15:
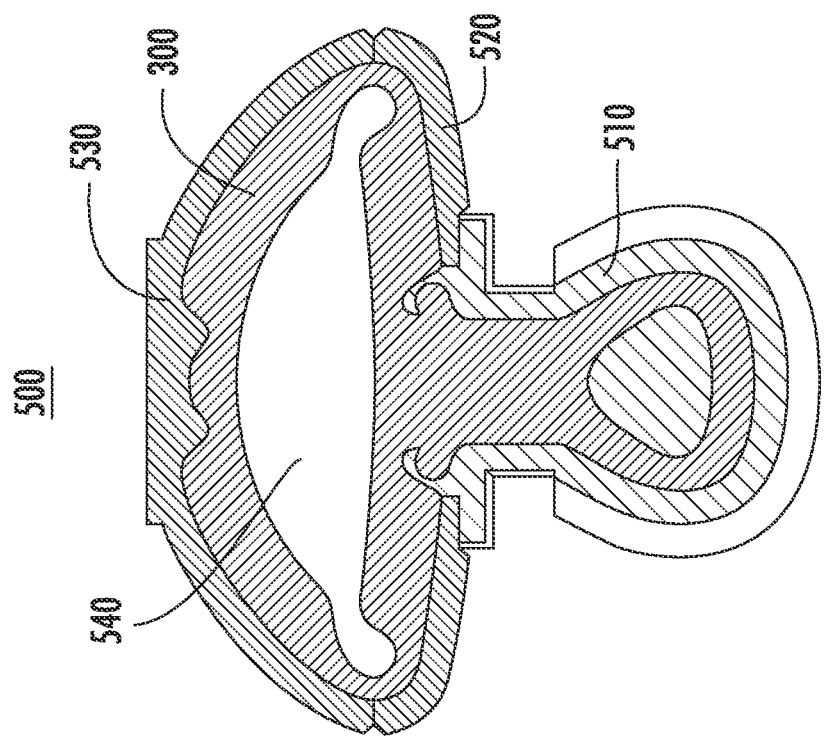
FIG. 15 is a cross-sectional view of the pessary of FIG. 4 being molded.
Figure 14:
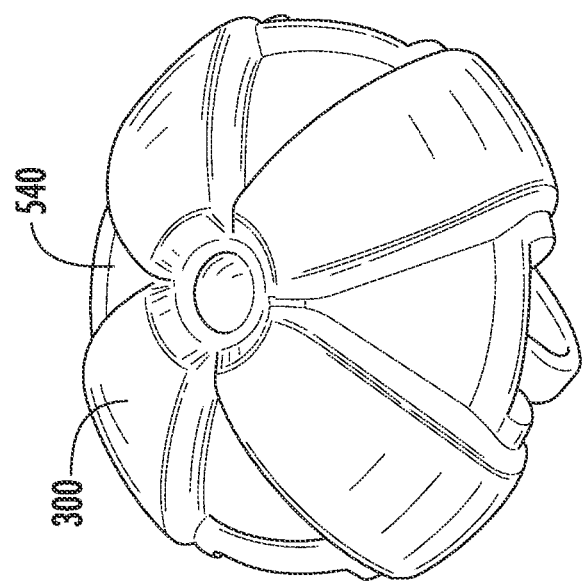
FIG. 14 is a top perspective view of the pessary of FIG. 4 with a unitary mold insert.

In some embodiments, as shown in FIGS. 10-12, a pessary 400 can further include webbing 450, 452 between respective supportive arm members 422a-422d where they come together at both the stem 410, proximate the lower hinge 426a and at the apex 428, proximate the top hinge 426c. For the sake of simplicity, the structure in pessary 400 can be assumed to be the same as pessary 300, with the addition of the webbing 450, 452, thus the remaining structure will not be discussed in detail again. The webbing 450, 452 can reenforce the respective support arm members 422a-422d to provide added structural integrity to the pessary 400. The webbing 450, 452 can reduce side to side movement of the petals 422a-422d, e.g. twisting of the petals, which can result in tearing of the pessary 400 or over collapsing one or more support members 422a-422d of the pessary 400, as shown in FIG. 13. This webbing 450, 452 is similar in concept to the thin membrane that can enclose the space between petals (as described in commonly owned U.S. patent application Ser. No. 16/832,839, incorporated by reference in its entirety herein). In this particular embodiment, the thin membrane, or "webbing" is only present near the top and bottom hinges 426c, 426a. Additionally, the webbing can be present in additional locations if needed.

In use, the pessary is designed to be inserted in the first elongated condition of FIG. 5, into the vagina to correct a prolapse. The first condition permits the device to comfortably be inserted. An applicator, not shown, with a barrel and a plunger may retain the pessary 300 in a compressed state for easier insertion to the patient. The plunger can be depressed after the applicator barrel and pessary 300 are inserted into the patient. When depressed, the plunger can eject the pessary 300 from the barrel and deploys the pessary 300 within the patient. Once the pessary 300 has been inserted to the correct position, an upward or distal force can be applied to the stem 310 to deploy the pessary to the second configuration for providing proper support of the prolapsed tissue, as shown in FIG. 7 for example, where the pessary 300 can remain until it is necessary for removal. During a removal step of the pessary 300, the user or practitioner can locate the removal feature 312 at the end of the stem 310 and apply a downward or proximal force to the stem 310. The downward force can cause the lower, center, and upper hinges 326a-326c of the pessary 300 to pivot to elongate and reduce the overall diameter of the support portion 320 of the pessary 300, as the pessary is being removed.

Figure 17:
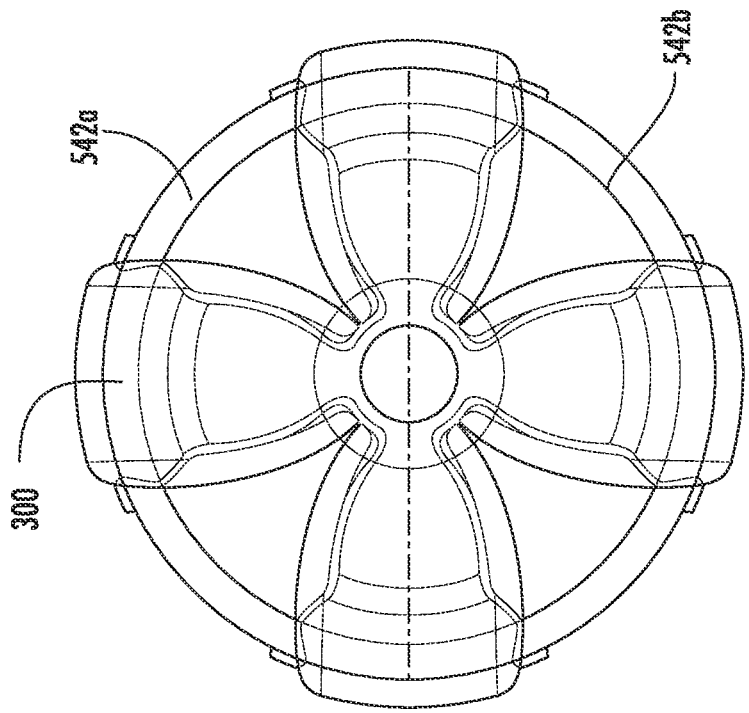
FIG. 17 is a top view of the pessary of FIG. 4 with a two part mold insert.
Figure 16:
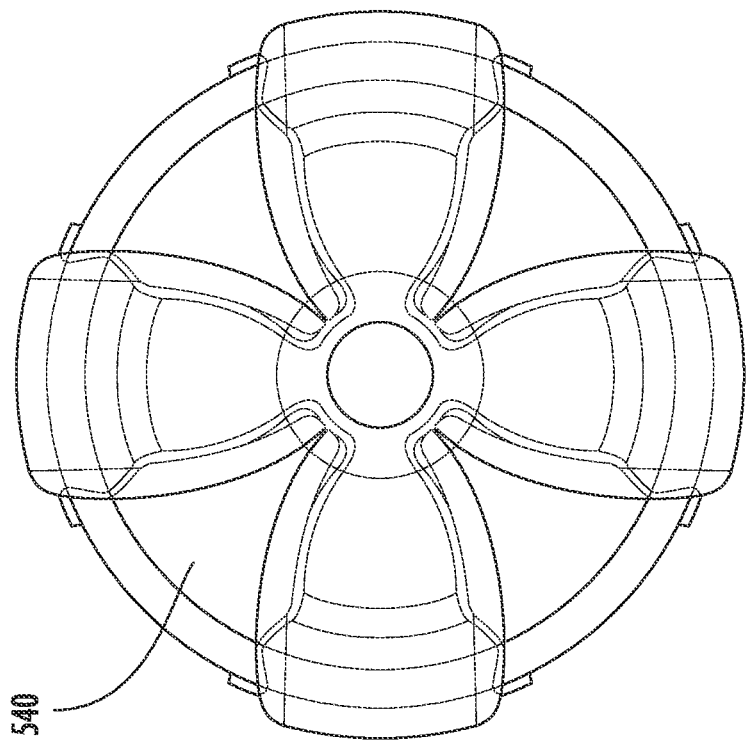
FIG. 16 is a top view of the pessary of FIG. 4 with a unitary mold insert.
Figure 18:
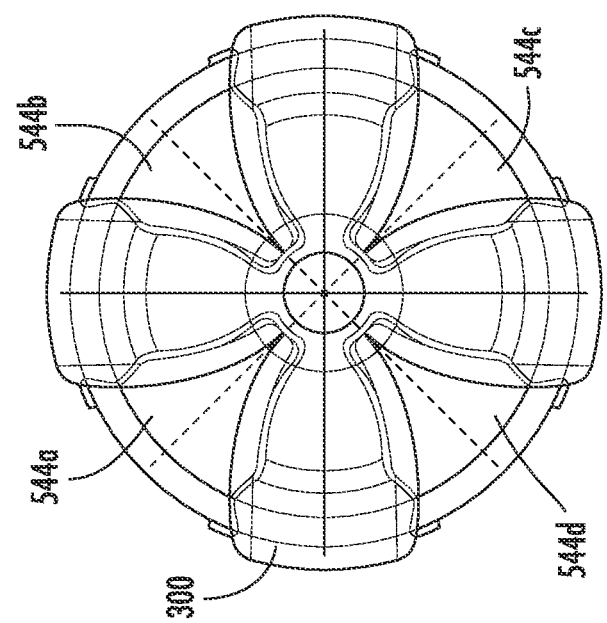
FIG. 18 is a top view of the pessary of FIG. 4 with a multi-piece mold insert.

As discussed above, in one preferred embodiment, the pessary 300 according to the present invention can be formed as a single, unitary, piece of material at the point of manufacturing, for example via a molding step. FIGS. 14-18 illustrate alternative embodiments of how the pessary of the present invention can be manufactured, such as by injection molding. In some embodiments, when the pessary 300 is manufactured as a single piece, as in FIGS. 14-16, a multi-piece mold 500 can create a negative of the pessary and can be filled with silicone, or other flowable material, typically using liquid injection molding or compression molding. The mold 500 can, as illustrated, include multiple pieces including a stem portion 510, a lower support portion 520, an upper support portion 530 and an insert 540. The mold 500 can contain a single insert piece 540 that fills the interior space inside the dome shape support portion 320 of the pessary 300. Once the injection molding is complete, and the pessary 300 is ready for removal, the single piece insert 540 can be removed upon the curing of the silicone. This one part insert 540 is illustrated in FIG. 16, for example. In some embodiments, the insert can be in two, or more, parts 542a, 542b to aid in removal, as shown in FIG. 17. The two parts of the insert 542a, 542b can be complimentary, or symmetrical pieces. In a further exemplary embodiment, the insert can be further broken up into more than 2 parts, such as four parts 544a, 544b, 544c, 544d, as seen in FIG. 18. The molds 540, 542a, 542b, 544a-d can be sandwiched between the upper mold portion 530 and the lower mold portion 520 where there are openings between the support members 322a-d of the pessary 300. It should be understood that FIGS. 14-18 show various embodiments of molding configurations, but the outside molds can be broken up in a myriad of ways and the insert can be a single part or numerous parts, and the parts can be broken up by a myriad of parting lines. All of these variations are considered to be part of and within the scope of the present invention.

Figure 19:
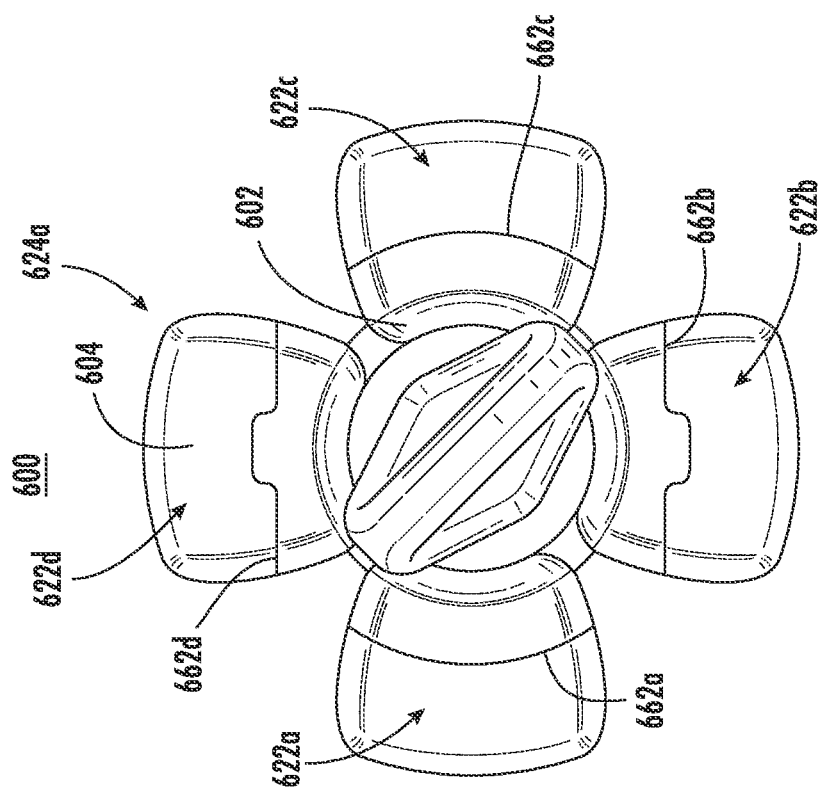
FIG. 19 is a bottom view of an alternative embodiment of the instant invention with alignment features.

In some embodiments, such as seen in FIG. 19, the pessary 600 can be manufactured in two separate parts 602, 604 and assembled together in a secondary manufacturing operation. In one embodiment, the parting lines 662a, 662b, 662c, 662d between the two pieces 602, 604 can be on the lower portion 624a of the respective support members 622a, 622b, 622c, 622d. The parting line 662a, 662c can be straight across on all support members, or the parting line 662b, 662d can incorporate a dovetail for alignment on all supportive members. Alternatively, as seen in FIG. 19, a combination of straight parting lines 662a, 662c and dovetail parting lines 662b, 662d can be used. The dovetail features 622b, 622d can align the two parts 602, 604 properly to aid in assembling and adhering the two parts together.

In another series of embodiments, as seen in FIGS. 20-25, similar to the embodiment of FIG. 19, the pessary can include two parts that can be split in the bottom section of the supportive arm in various ways. Advantageously, one part can contain an external facing half of the bottom portion of the supportive arm and the other portion contains the internal facing half of the bottom portion of the supportive arm and the stem. These two pieces can be adhered, connected, chemically welded, or secured together with, for example, a silicone adhesive, glue or the like. In these two piece embodiments, various alignment features can be provided to help to align the two parts during assembly, thus providing for a more accurate manufacturing process. The alignment features themselves can have a number of different alternatives. These alternatives can include a clearance fit, be "line-to-line," or even have an interference fit, i.e. the male feature can be smaller than, flush with, or oversized compared to the female feature. The illustrated embodiments make use of a tighter fit that can allow the two parts to stay together during assembly, reducing the need to be held together by an external fixture while the adhesive cures.

Figure 21:
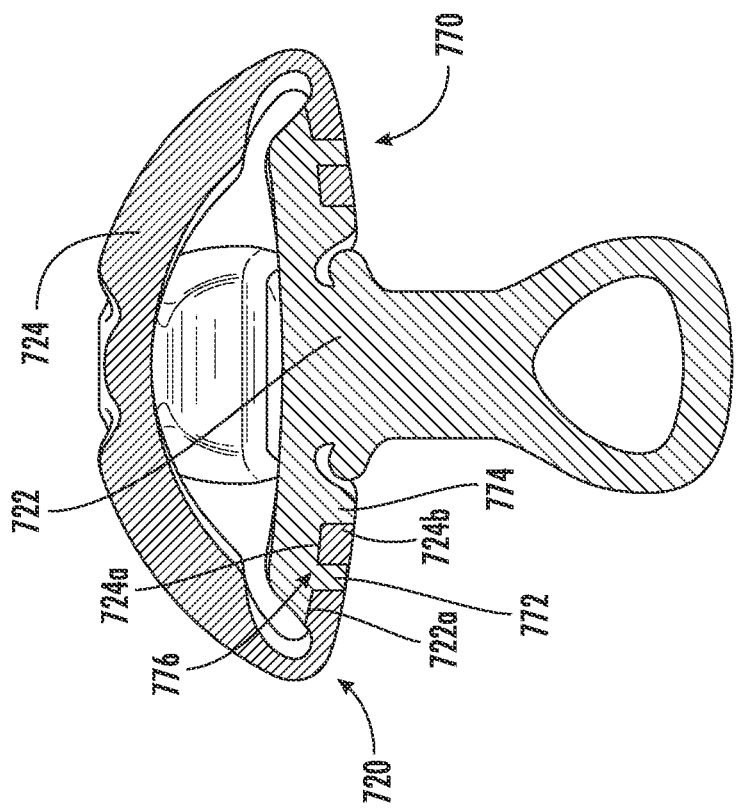
FIG. 21 is a cross-sectional view of the pessary of FIG. 20.
Figure 20:
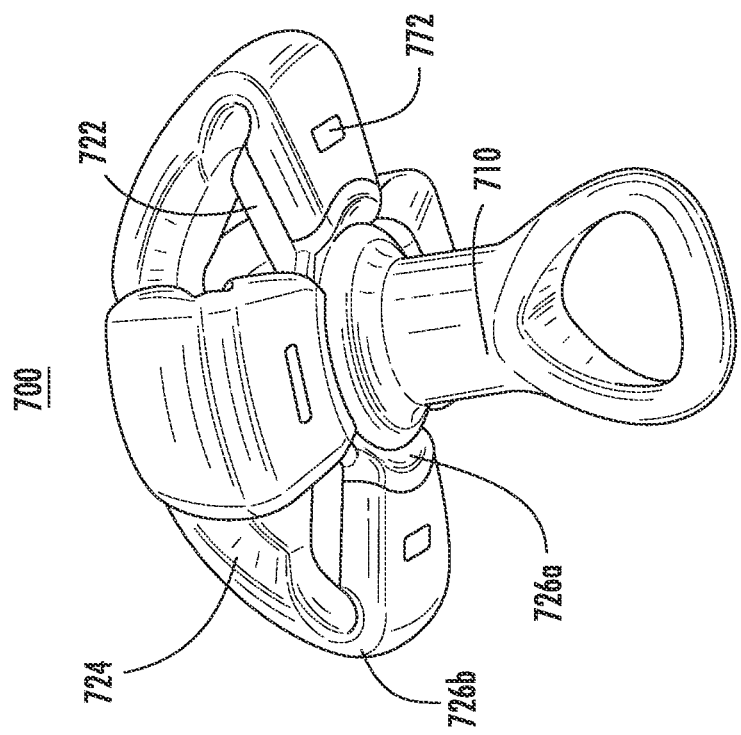
FIG. 20 is a bottom perspective view of an alternative embodiment of the instant invention with alignment features.

In one example, as shown in FIGS. 20 and 21, the pessary 700 can include a first support portion 722 and a second support portion 724. The two support portions 722, 724 can be secured together using various adhesives or other mechanical or chemical fasteners. Advantageously, the embodiment includes a notched connection 770 to ensure proper alignment between the two pieces. For the sake of ease, the following discussion will only focus on a single support member 720 connection, though the connection can be the same for each respective support member. The support portion can include a first support portion 722 connected to the stem 710 portion via the lower hinge 726a and a second support portion 724 connected to the upper support portion via the center hinge 726b. The first support portion 722 can include an outer face 722a that is radially outward facing in the first orientation and face the stem in the second configuration. The outer face of the first support portion can include a protrusion 772 that extends outward from a central area of the outer face 722a and a ridge 774 on a lower end of the outer face 722a, closer to the lower hinge 726a. The protrusion 772 is shown as a having a rectangular shape, though other cross section shapes can be used as needed. The second support portion 724 can include an inner face 724a that is sized and shaped to be received by the outer face 722a of the first support portion 722. A face 724b of the second support portion 724 can abut the ridge 774 of the first support portion 722 and the second support portion 724 can include an opening 776 that is sized to receive the protrusion 772 of the first support portion 722. In some embodiments, the opening 776 can be slightly smaller than the protrusion 772 to create an interference fit. As each of the support members includes these alignment features, each of the four support members will ensure proper alignment of the first and second support portions relative to each other.

Figure 23:
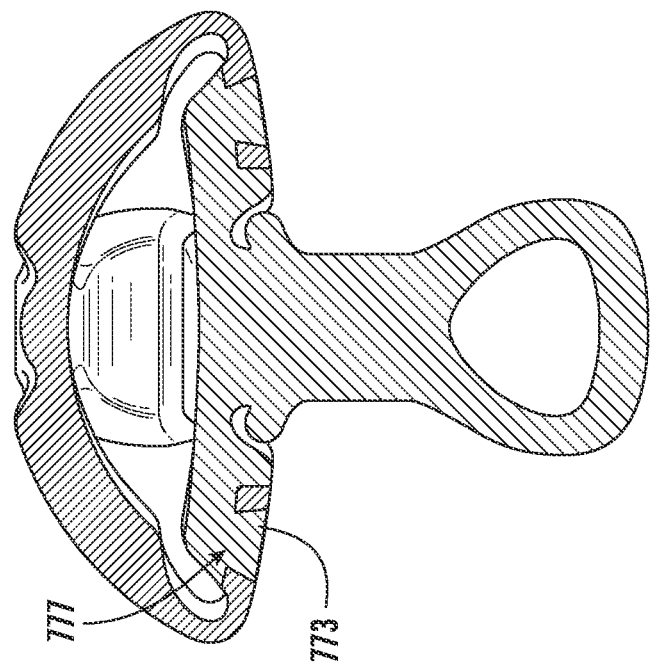
FIG. 23 is a cross-sectional view of the pessary of FIG. 22.
Figure 22:
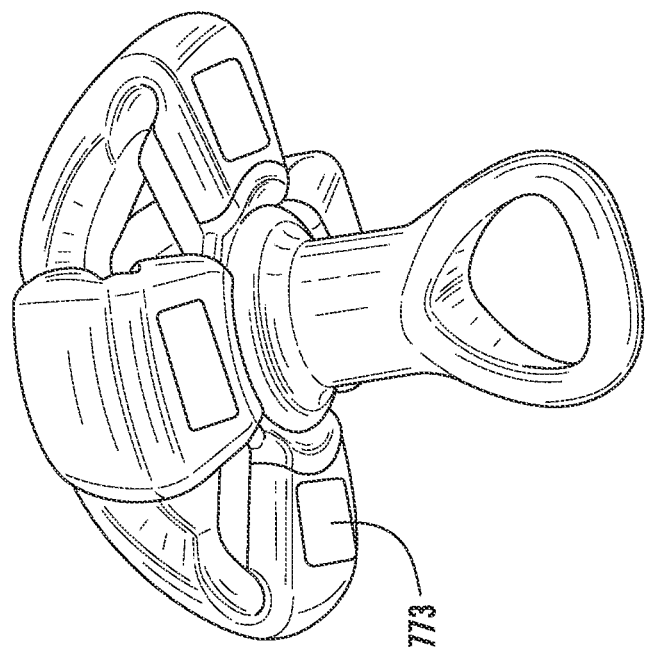
FIG. 22 is a bottom perspective view of an alternative embodiment of the instant invention with alternative alignment features.
Figure 25:
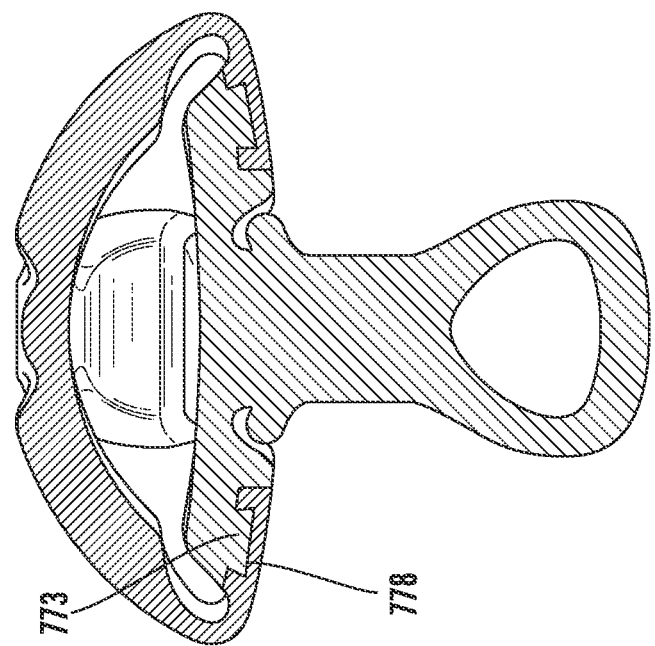
FIG. 25 is a cross-sectional view of the pessary of FIG. 24.
Figure 24:
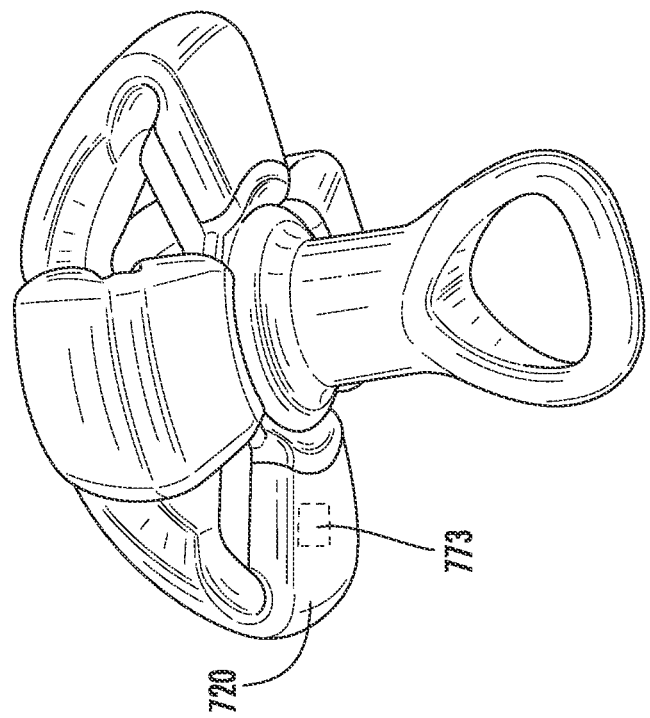
FIG. 24 is a bottom perspective view of an alternative embodiment of the instant invention with further alternative alignment features.

Alternatively, the alignment features can include an undercut protrusion 773 as shown in FIGS. 22 and 23. The undercut protrusion 773 geometry provides for a trapezoidal cross section, as seen in FIG. 23, to hold the two parts together during assembly. In the embodiment of FIGS. 22 and 23, the female alignment feature 777 can be a through-hole, where the male alignment feature 775 would be visible on the outside surface of the pessary as shown in FIG. 22. Alternatively, as seen in FIGS. 24 and 25, the female alignment feature 778 can be a pocket, or a partial bore that does not extend through the entire thickness of the support member 720, where the male alignment feature 773 does not go all the way through the other part and is thus not visible, as seen in FIGS. 24 and 25.

Figure 27:
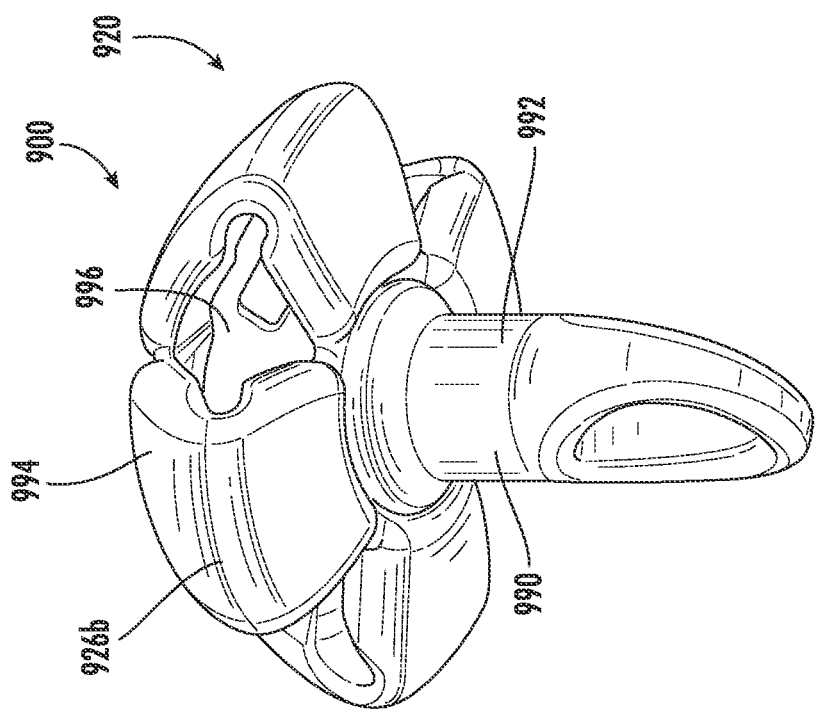
FIG. 27 is bottom perspective view of the alternative embodiment of FIG. 26 showing mold parting lines.
Figure 26:
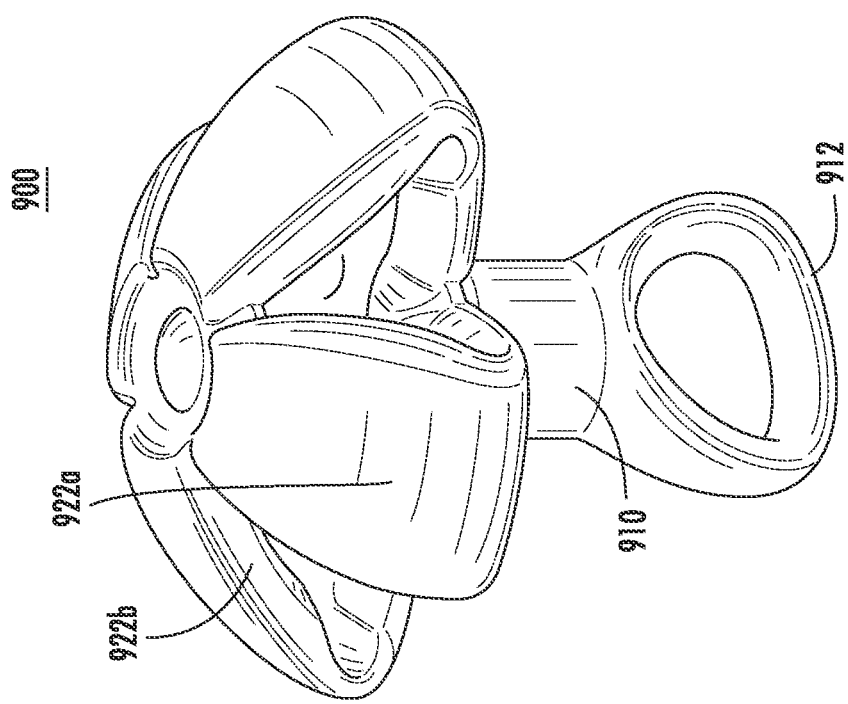
FIG. 26 is a top perspective view of an alternative embodiment of the present invention.
Figure 28:
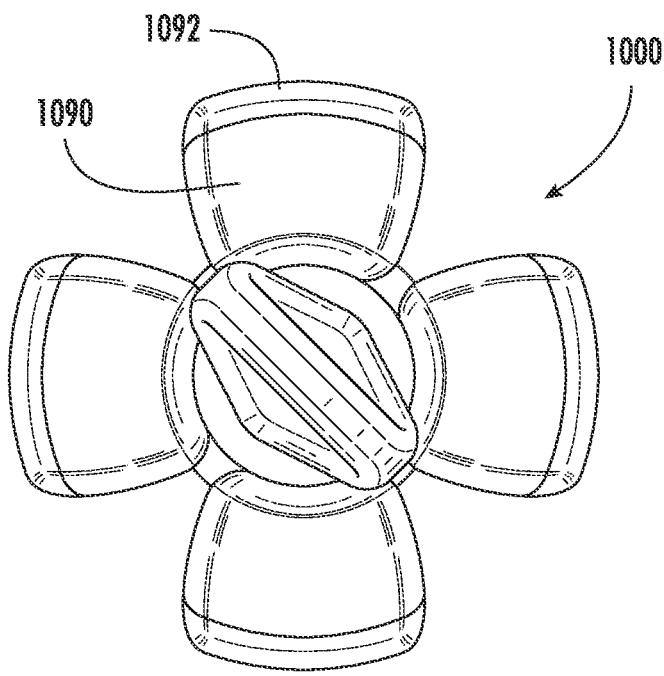
FIG. 28 is a bottom view of a further alternative embodiment.

In some embodiments the stem 910 is rotated so that the finger loop 912 can be oriented so that the loop is at an approximately 45 degree angle between support members 922a, 922b, as shown in FIG. 26 and additionally similar to the bottom view of FIG. 28. This alternative arrangement can enable alternative mold configurations. FIG. 27 illustrates one such possible mold configuration. For the sake of ease, the mold itself is not illustrated, rather the location of each piece of the mold are demarcated on the respective surfaces of the pessary 900. In the illustrated embodiment, a first lower part 990 of the mold and a second lower part 992 of the mold can be split along the line shown that extends parallel to a longitudinal axis of the stem 910 up till approximately the central hinge 926b where a third piece 994 of the mold extends over the upper portion of the support members. As with the other embodiments, a single or multi-piece insert 996 can be inserted in the cavity of the support member 920. This particular mold configuration can allow the final molded pessary 900 to not have visible markings or flash from where the mold parts are separated in highly visible surfaces on the pessary.

Figure 29:
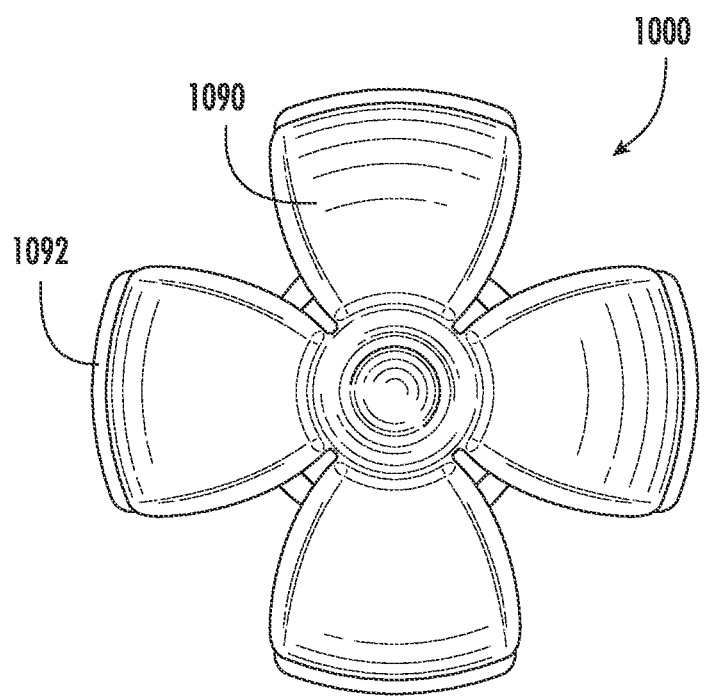
FIG. 29 is a top view of the embodiment of FIG. 28.

The pessary device of the present invention can be made of known materials that are suitable for pessary devices, such as silicone with or without inserts made of nylon or other rigid material, as discussed in detail above. As shown in FIGS. 28 and 29, such rigid inserts 1090 are configured to prevent various components of the pessary 1000 of the present invention from being too stretchy or to minimize the possibility of tearing of the silicone portion 1092. The pessary of the present invention can also be made out of silicone that is a different durometer from the supportive portion of the pessary to either increase rigidity or flexibility of pessary, as discussed above.

It would be appreciated by those skilled in the art that various changes and modifications can be made to the illustrated embodiments without departing from the spirit of the present invention. All such modifications and changes are intended to be covered by the appended claims.

What is claimed is:

1. A pessary device, comprising:
   a stem;
   a plurality of support members hingedly connected to the stem; wherein each of the plurality of support members include an upper support portion and a lower support portion hingedly connected to each other by a central hinge, the lower support portion being hingedly connected to the stem with a respective lower hinge;
   a ridge circumferentially located about the stem; wherein the ridge contacts an outer face of the lower support portion and prevents the lower support portion from rotating past a predetermined position;
   whereby the ridge provides a stop to prevent pivoting of the support members past the predetermined position.

2. The pessary device of claim 1,
   wherein the pessary is made of a first material and a second material, and
   wherein the first material is more rigid than the second material.

3. The pessary device of claim 1, wherein the respective upper support portions are connected to a top apex portion by a respective upper hinge.

4. The pessary device of claim 1, wherein there is webbing arranged between each of the respective support members.

5. The pessary device of claim 1, wherein the respective lower hinges are fixed at a height on the stem above the ridge.

6. The pessary device of claim 1, wherein the pessary is a unitary piece of material.

7. The pessary device of claim 1, wherein the stem and the plurality of support members are formed of at least two distinct parts.

8. The pessary device of claim 1,
   wherein, in a first condition the support members have a first height and a first outer diameter, wherein, in a second condition the support member have a second height and a second outer diameter, and wherein the first height is greater than the second height and the first outer diameter is smaller than the second outer diameter.

9. The pessary device of claim 8, wherein the support members have an intermediate condition between the first condition and the second condition, and in the intermediate condition the support members have a third height and a third outer diameter, wherein the third height is less than the first height and greater than the second height, and wherein the third outer diameter is greater than both the first and second outer diameters.

10. The pessary device of claim 1, further comprising webbing extending between respective neighboring supportive members of the plurality of support members.

11. The pessary device of claim 1, wherein the plurality of supportive members is four supportive members.

12. The pessary device of claim 11, wherein the four supportive members are equally spaced circumferentially about the stem.

13. A pessary, comprising:

a stem;

a circumferential ridge extending radially outward from the stem at a distal end of the stem; and a support member including a plurality of support member petals, wherein each support member petals includes an upper support member and a lower support member, where the upper and lower support members are attached together via a central hinge and the lower support member attaches to the stem via a lower hinge;

wherein the circumferential ridge contacts an outer face of the respective lower support members and prevents the lower support members from rotating past a predetermined position.

14. The pessary of claim 13, wherein, in a first configuration the support member has a first height and a first outer diameter, wherein, in a second configuration the support member has a second height and a second outer diameter, and wherein the first height is greater than the second height and the first outer diameter is smaller than the second outer diameter.

15. The pessary device of claim 14, wherein the support member has an intermediate configuration between the first configuration and the second configuration, and in the intermediate configuration the support member has a third height and a third outer diameter, wherein the third height is less than the first height and greater than the second height, and wherein the third outer diameter is greater than both the first and second outer diameters.

16. The pessary device of claim 13, wherein the respective lower hinges are fixed at a height on the stem above the circumferential ridge.

\* \* \* \* \*